US Patent Number: 4,587,052
Date of Patent: May 6, 1986

Ueda et al.

[54] 1H-PYRROLO-[2,1-C][1,4]BENZODIAZE-PINE-2-ACRYLAMIDE COMPOUNDS HAVING ANTITUMOR ACTIVITY

[75] Inventors: Yasuo Ueda, Hirakata; Yusei Shiraga, Kobe; Satoshi Morimoto, Nagaokakyo; Yoshio Kagitani, Kashihara, all of Japan; Satoshi Funakoshi, Los Angeles, Calif.; Tadakazu Suyama, Tsuzuki, Japan

[73] Assignee: The Green Cross Corporation, Osaka, Japan

[21] Appl. No.: 578,032

[22] Filed: Feb. 8, 1984

[30] Foreign Application Priority Data

Feb. 10, 1983 [JP] Japan .................................. 58-20798
Feb. 28, 1983 [JP] Japan .................................. 58-31980

[51] Int. Cl.[4] .......................................... C07D 487/04
[52] U.S. Cl. ............................................. 260/239.3 T
[58] Field of Search ....................... 260/245.7, 239.3 T

[56] References Cited

U.S. PATENT DOCUMENTS

| | | | |
|---|---|---|---|
| 3,361,742 | 1/1968 | Berger et al. | 260/239.3 T |
| 3,523,941 | 8/1970 | Leimgruber et al. | 260/239.3 T |
| 3,524,849 | 8/1970 | Batcho et al. | 260/239.3 T |
| 3,763,183 | 10/1973 | Carabateas | 260/245.7 |
| 4,011,140 | 3/1977 | Komatsu | 435/119 |
| 4,185,016 | 1/1980 | Takanabe et al. | 260/239.3 T X |
| 4,309,437 | 1/1982 | Ueda et al. | 260/239.3 T X |

FOREIGN PATENT DOCUMENTS 53-082792  7/1978  Japan .............................. 260/245.7

OTHER PUBLICATIONS

Leimgruber, et al., J. Am. Chem. Soc., vol. 87 (24), 1965, pp. 5793-5795.
March, ed., Advanced Organic Chemistry, 2nd ed., McGraw-Hill, N.Y., (1970), pp. 358-359.
"Communications to the Editor", Journal of American Chemical Society, 87:24, Dec. 20, 1965, pp. 5791-5795.
Hurley, "Pyrrolo(1,4)Benzodiazepine Antitumor Antibiotics, Comparative Aspects of Anthramycin, Tomaymycin and Sibiromycin," Review Article, J. Antibiotics, vol. 30, No. 5, pp. 349-370.

Primary Examiner—Donald G. Daus
Assistant Examiner—William A. Teoli, Jr.
Attorney, Agent, or Firm—Cushman, Darby & Cushman

[57] ABSTRACT

Benzodiazepine derivative represented by the following general formula or pharmaceutically acceptable salt thereof:

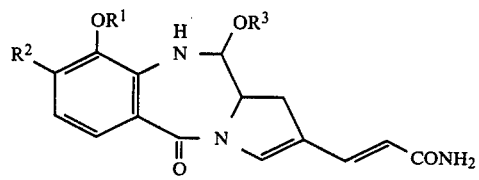

wherein $R^1$ is —$COR^4$ ($R^4$ is a carboxylic acid residue) or an alkyl or aralkyl group (these groups have a substituent selected from a carboxyl group, an amino group and a cyano group), $R^2$ is a lower alkyl group and $R^3$ is a hydrogen atom or a lower alkyl group.

The above compound is low in toxicity and has an antitumor activity.

19 Claims, No Drawings

1H-PYRROLO-[2,1-C][1,4]BENZODIAZEPINE-2-ACRYLAMIDE COMPOUNDS HAVING ANTITUMOR ACTIVITY

This invention relates to novel a benzodiazepine derivative and more particularly to novel 1H-pyrrolo[2,1-C][1,4]benzodiazepine-2-acrylamide compound having an antitumor activity.

It has already been known that (a) compound represented by the general formula

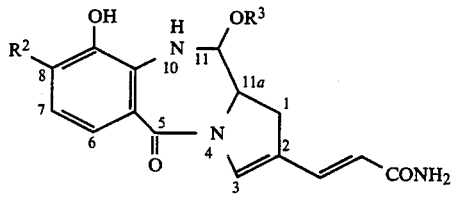

($R^2$ is a lower alkyl group and $R^3$ is a hydrogen atom or a lower alkyl group), for example, 5,10,11,11a-tetrahydro-9,11-dihydroxy-8-methyl-5-oxo-1H-pyrrolo-[2,1-C][1,4]-benzodiazepine-2-acrylamide (hereinafter referred to as PBA) and (b) 5,11,11a-trihydro-9-hydroxy-8-methyl-5-oxo-1H-pyrrolo-[2,1-C][1,4]benzodiazepine-2-acylamide (hereinafter referred to as P'B'A') represented by the general formula

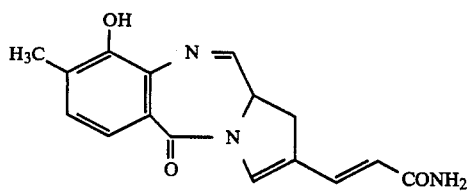

have an antibacterial activity and an antitumor activity. It has also been known already that PBA is produced as a metabolite when *Streptomyces spadicogriseus KOMATSU FERM* P-3275, ATCC 31179 or *Streptomyces refuineus var. thermotolerans*, NRRL 3143, or NRRL 3144 is cultured and P'B'A' is derived from PBA. (Japanese Patent Application Kokai (Laid-open) No. 79,082/1977; U.S. Pat. No. 3,361,742; J. Amer. Chem. Soc., 87, 5791-5793; J. Antibio., 30, 349-370).

However, the above compounds exhibit strong side effects in acute toxicity, local impairment, etc. and further their relatively low solubility in water makes it difficult to use the compounds in the form of an injection. As a consequence, these compounds are not yet in general use as drugs. In view of such a situation, the present inventors made various studies with an aim of obtaining derivatives of the above compounds which are low in toxicity and local impairment and soluble in water. As a result, there have been successfully obtained benzodiazepine derivatives having a higher therapeutic index (toxic dose/effective dose) than the above compounds, being stable, and represented by the general formula (III) given later. Based on this success, the present invention has been completed.

An object of this invention is to provide a novel benzodiazepine derivative low in toxicity, having an antitumor activity and usable as an injection.

Other objects and advantages of the present invention will be made clear by the following description.

According to the present invention, there are provided a benzodiazepine derivative represented by the following general formula or pharmaceutically acceptable salt thereof:

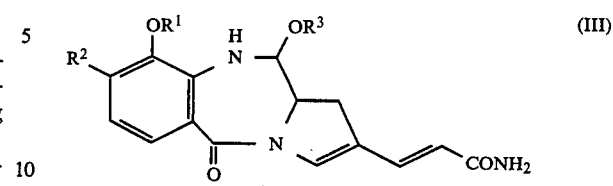

wherein $R^1$ is $-COR^4$ ($R^4$ is a carboxylic acid residue) or an alkyl or aralkyl group (these groups have a substituent selected from a carboxyl group, an amino group and a cyano group), $R^2$ is a lower alkyl group and $R^3$ is a hydrogen atom or a lower alkyl group.

In the general formula (III), the carboxylic acid residue represented by $R^4$ is preferably those having a carboxyl group at their ends. Its examples are groups represented by $-Y-COOH$ and $-Y'-O-Y''-COOH$ (Y, Y' and Y'' each are an alkylene or phenylene group). Here, the alkylene group has a straight or branched chain and preferably 1 to 15 carbon atoms and more preferably 1 to 11 carbon atoms. Its examples are methylene, ethylene, propylene, trimethylene, butylene, tetramethylene, etc. These carboxylic acid residues may have a substituent such as, for example, nitro or acylmercapto (the acyl includes those of $C_2$ to $C_5$, preferably acetyl, propionyl and butyryl, etc.). The lower alkyl group is preferably those of 1 to 4 carbon atoms. Its examples include methyl, ethyl, n-propyl, iso-propyl, n-butyl, iso-butyl, etc.

In the general formula (III), the alkyl group represented by $R^1$ has a straight or branched chain and preferably 1 to 8 carbon atoms (for example, methyl, ethyl, n-propyl, iso-propyl, n-butyl, iso-butyl, n-pentyl, n-hexyl, 3-ethylpropyl, n-heptyl, etc.) and more preferably 2 to 6 carbon atoms. The substituents of these alkyl groups may be either of carboxyl, amino and cyano.

The aryl moiety of the aralkyl group represented by $R^1$ is preferably phenyl. The alkylene moiety has a straight or branched chain and 1 to 4 carbon atoms (for example, methylene, ethylene, trimethylene, propylene, etc.) and preferably 1 to 2 carbon atoms. The substituents of these aralkyl groups may be either of carboxyl, amino and cyano and is preferably amino or cyano.

The pharmaceutically acceptable salt of the benzodiazepine derivative represented by the general formula (III) include, for example, a salt of an alkali metal (sodium, potassium or the like) as well as a salt of an alkaline earth metal (calcium or the like), when the derivative contains a carboxyl group.

The compound represented by the general formula (III) and a salt thereof has the following characteristics. (1) An antitumor activity. (2) Far weaker acute toxicity than the compound (I) and high safety. (3) Soluble in water very easily (solubility at room temperature: 1 g/ml). (4) When injected in the form of an aqueous solution, they give only a little pain and local impairment. (5) More stable than the compound (I), in the state of powder and also of an aqueous solution, whereby coloring can be prevented effectively.

The compound represented by the general formula (III) according to the present invention wherein $R^1$ is $-COR^4$ can be obtained, for example, by reacting a compound represented by the general formula (I) with a cyclic acid anhydride preferably in the presence of a basic or acidic catalyst. The cyclic acid anhydride includes alicyclic acid anhydrides (for example, succinic acid anhydride, glutaric acid anhydride, adipic acid anhydride, nonenylsuccinic acid anhydride, diglycolic acid anhydride, sacetylmercaptosuccinic acid anhydride) and their derivatives, aromatic acid anhydrides (for example, phthalic acid anhydride, nitrophthalic acid anhydride) and their derivatives, etc. The cyclic acid anhydride can be used in an amount of 1 to 50 molar equivalents relative to a phenol group at the 9-position of the compound (I).

The basic catalyst includes pyridine compounds (pyridine, 4-dimethylaminopyridine, 4-pyrrolidinopyridine, etc.), triethylamine, etc. These compounds are generally used as a reaction solvent in molar equivalents of a large excess relative to the compound (I). The acidic catalyst includes p-toluenesulfonic acid, zinc chloride, sulfuric acid, etc. These compounds are used generally in an amount of 1 to 2 molar equivalents relative to the compound (I) and, in this case, there is separately used, as a reaction solvent, an organic solvent such as, for example, acetonitrile, dimethylformamide, dimethyl sulfoxide and the like.

The reaction proceeds in the temperature range of 0° to 100° C. for 1 to 30 hours. Generally, 0° to 30° C. is used when a basic catalyst is employed and 80° to 100° C. is used when an acid catalyst is employed.

The reaction product obtained according to the above process can be collected, after completion of the reaction, from the reaction mixture by usual physical and chemical methods such as concentration, precipitation, deposition, chromatography and the like.

The thus obtained compound can be further converted to a salt at the carboxyl group of $R^1$, by a usual method. For example, by stirring the above obtained compound together with 1 molar equivalent of a lower alkoxide of an alkali or alkaline earth metal salt in a lower alkanol such as methanol, ethanol or the like for 20 min at 15 to 30° C., there can be obtained a corresponding alkali or alkaline earth metal salt of the above compound. This salt can be collected by the use of usual physical and chemical methods such as concentration, precipitation, deposition, chromatography and the like.

The compounds represented by the general formula (III) according to the present invention wherein $R^1$ is an alkyl or aralkyl group can be produced by reacting a compound represented by the general formula (I) with a compound represented by the general formula $$R^1-X \qquad (IV)$$

wherein $R^1$ has the same definition as given above and X is a halogen atom.

In the general formula (IV), the halogen atom represented by X includes chlorine, bromine, and iodine.

The reaction is conducted generally in the presence of a basic solvent [an aqueous solution of an inorganic alkali such as an alkali metal hydroxide, an alkaline earth metal hydroxide or the like (for example, sodium hydroxide, potassium hydroxide, calcium hydroxide); a solution of an organic alkali such as tributylamine, pyridine, 4-dimethylaminopyridine, tripropylamine or the like; a mixture thereof; etc.]or a basic catalyst (for example, an alkoxide of an alkali or alkaline earth metal such as sodium, calcium or the like).

The compound (IV) is used generally in an amount of 1 to 50 molar equivalents relative to 1 mole of the compound represented by the general formula (I).

The reaction proceeds in the temperature range of 20 to 100° C. for 1 to 30 hours.

The reaction product obtained according to the above process can be collected, after completion of the reaction, from the reaction mixture by usual methods such as concentration, precipitation, deposition, chromatography and the like. Of the thus obtained compounds, for example, those having a free carboxyl group can be converted to the corresponding alkali or alkaline earth metal salts by a usual method, namely, by stirring together with 1 to 1.2 molar equivalents of a lower alkoxide of an alkali or alkaline earth metal for 10 to 20 min at 15° to 30° C. in a lower alcohol such as methanol, ethanol or the like or in an aqueous solution. These alkali or alkaline earth metal salts can be collected by usual methods such as concentration, deposition, precipitation, chromatography and the like.

Next, specific examples of the benzodiazepine derivatives of the present invention are shown. Examples of the compounds of the general formula (III) wherein $R^1$ is —$COR^4$ are as follows.

5,10,11,11a-Tetrahydro-9-(3-carboxypropanoyloxy)-11-hydroxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(4-carboxybutanoyloxy)-11-hydroxy-8-methyl-5-oxo-1H-pyrrolo-[2,1-C][1,4]-benzodiazepine-2-acrylamide, and its alkali and alkaline earth metal satls 5,10,11,11a-Tetrahydro-9-(5-carboxypentanoyloxy)-11-hydroxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(3-carboxypentanoyloxy)-11-hydroxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(4-carboxy-3-oxabutanoyloxy)-11-hydroxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(3-carboxy-3-S-acetylmercaptopropanoyloxy)-11-hydroxy-8-methyl-5-oxo-1H-pyrrolo[2,1-C][1,4]-benzodiazepine-2-acrylamide, and its alkali and alkaline earth metal salts 5,10,11,11a-Tetrahydro-9-(2-carboxyphenylcarbonyloxy)-11-methoxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(2-carboxy-3-nitrophenylcarbonyloxy)-11-methoxy-8-methyl-5-oxo-1H-pyrrolo[2,1-C][1,4]-benzodiazepine-2-acrylamide, and its alkali and alkaline earth metal salts Examples of the compounds of the general formula (III) wherein $R^1$ is an alkyl or aralkyl group are as follows.

5,10,11,11a-Tetrahydro-9-(3-aminopropoxy)-11-hydroxy-8-methyl-5-oxo-1H-pyrrolo-[2,1-C][1,4]benzodiazepine-2-acrylamide, and its alkali and alkaline earth metal salts 5,10,11,11a-Tetrahydro-9-(4-amino-1-ethylpropoxy)-11-methoxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(2-cyanoethoxy)-11-hydroxy-8-methyl-5-oxo-1H-pyrrolo-[2,1-C][1,4]benzodiazepine- 2-acrylamide, and its alkali and alkaline earth metal salts 5,10,11,11a-Tetrahydro-9-(3-cyanopropoxy)-11-hydroxy-8-methyl-5-oxo-1H-pyrrolo-[2,1-C][1,4]benzodiazepine-2-acrylamide, and its alkali and alkaline earth metal salts 5,10,11,11a-Tetrahydro-9-(2-cyanobenzyloxy)-11-hydroxy-8-methyl-5-oxo-1H-pyrrolo-[2,1-C][1,4]benzodiazepine-2-acrylamide and its alkali and alkaline earth metal salts 5,10,11,11a-Tetrahydro-9-carboxymethoxy-11-methoxy-8-methyl-5-oxo-1H-pyrrolo-[2,1-C][1,4]-benzodiazepine-2-acrylamide, and its alkali and alkaline earth metal salts 5,10,11,11a-Tetrahydro-9-(2-carboxyethoxy)-11-methoxy-8-methyl-5-oxo-1H-pyrrolo-[2,1-C][1,4]benzodiazepine-2-acrylamide, and its alkali and alkaline earth metal salts 5,10,11,11a-Tetrahydro-9-[2-(4-carboxyphenyl)ethoxy]-11-methoxy-8-methyl-5-oxo-1H-pyrrolo-[2,1-C][1,4]-benzodiazepine-2-acrylamide, and its alkali and alkaline earth metal salts In general, the compounds represented by the general formula (III) according to the present invention have higher solubility in water when they are converted to salts, particularly alkali or alkaline earth metal salts.

The benzodiazepine derivatives represented by the general formula (III) according to the present invention were subjected to toxicity and antitumor activity tests in order to confirm their usefulness. The test results are shown in Tables 1 and 2.

The following test methods were used.

Toxicity test

A test compound was dissolved in dimethyl sulfoxide and the solution was diluted to 50-fold with a physiological saline solution. This original solution was serially diluted at a common ratio of 1.15. Each resulting solution was administered intraperitoneally to groups of 10 to 15 dd-strain male mice, each 18 to 20 g in body weight. The mice were then bred on a usual diet and water and their survival was observed for 3 weeks. The $LD_{50}$ was calculated from the number of dead mice of each group according to the Probit method.

Antitumor activity test $10^6$ Cells of mouse ascitic leukemia p388 were administered intraperitoneally into each member of the groups of 8 to 12 $BDF_1$-strain male mice, each 18 to 20 g in body weight. After 24 hr from the administration, a test compound was intraperitoneally administered to each member of the test group in a predetermined dose once a day for 4 consecutive days. Days elapsed until death of the test animal were counted for each mouse. To each member of the control group, a physiological saline solution was administered. The average survival period of the animal was represented by mean survival time. The prolongation of survival time, indicative of the effectiveness of a test compound, was calculated by the following equation.

Prolongation of survival time, % =

$$\left( \frac{\text{Mean survival time of the test group}}{\text{Mean survival time of the control group}} - 1 \right) \times 100$$

The therapeutic index was calculated by the following equation.

Therapeutic index =

$$\frac{LD_{50}}{\text{Total amount of a test compound administered until prolongation of survival time reaches 50\%}}$$

TABLE 1

| General formula (III) R¹ | R² | R³ | $LD_{50}$ (mg/kg) | Antitumor activity Daily dose (mg/kg) | Prolongation of survival time, % |
|---|---|---|---|---|---|
| —CO—CH₂CH₂—COOK | CH₃ | H | 120.4 | 30 | 160 |
| —CO—CH₂CH₂CH₂—COOK | CH₃ | H | 150.6 | 30 | 185 |
| —CO—CH₂CH₂CH₂CH₂—COOK | CH₃ | H | 156.8 | 30 | 172.5 |
| —CO—CH₂—CH(C₉H₁₉)—COONa | CH₃ | H | 122.2 | 30 | 131.6 |
| —CO—CH₂—O—CH₂—COOK | CH₃ | H | 160.1 | 30 | 181.2 |
| —CO—CH₂—CH(SCOCH₃)—COONa | CH₃ | H | 138.2 | 30 | 172.5 |
| —CO—C₆H₄—COONa | CH₃ | CH₃ | 86.9 | 30 | 130.2 |
| —CO—C₆H₃(NO₂)—COONa | CH₃ | CH₃ | 95.0 | 30 | 152 |
| PBA | | | 0.73 | 0.1 | 127.8 |

TABLE 2

| General formula (III) R¹ | R² | R³ | $LD_{50}$ (mg/kg) | Antitumor activity Daily dose (mg/kg) | Prolongation of survival time, % | Therapeutic index |
|---|---|---|---|---|---|---|
| —(CH$_2$)$_3$NH$_2$ | CH$_3$ | H | 103.4 | 10 | 192 | 93.5 |
| —CH(CH$_2$—CH$_3$)—(CH$_2$)$_3$NH$_2$ | CH$_3$ | CH$_3$ | 115.2 | 10 | 184 | 78.4 |
| —(CH$_2$)$_2$CN | CH$_3$ | H | 118.4 | 10 | 197 | 103.8 |
| —(CH$_2$)$_3$CN | CH$_3$ | H | 110.5 | 10 | 188 | 95.2 |
| —CH$_2$-(2-CN-phenyl) | CH$_3$ | H | 120.3 | 10 | 154 | 73.3 |
| —CH$_2$COONa | CH$_3$ | CH$_3$ | 102.3 | 10 | 228 | 88.5 |
| —CH$_2$CH$_2$COOK | CH$_3$ | CH$_3$ | 105.4 | 10 | 172 | 72.4 |
| —CH$_2$CH$_2$-(4-COOH-phenyl) | CH$_3$ | CH$_3$ | 128.5 | 10 | 165 | 82.3 |
| PBA | CH$_3$ | | 0.73 | 0.1 | 118 | 36.5 |

The compounds (III) of the present invention and their pharmaceutically acceptable salts have an antitumor activity to mammals such as humans, horses, sheeps, rats, mice and the like and can be used as an antitumor agent.

The compounds (III) and their low-toxic salts can be processed together with a proper carrier into drugs such as tablets, capsules, injections and the like by known methods and are administered orally or parenterally. The compounds (III) and their low-toxic salts are soluble particularly in water and stable even in the form of an aqueous solution, therefore, are made into injections very easily. The compounds (III) and their salts can be administered generally in an amount of 100 to 5000 mg/adult body/day, and when they are intravenously injected for the purpose of curing general malignant tumors such as stomach cancer, lung cancer, leukemia and the like, they are administered in an amount of 20 to 1000 mg/adult body/day.

The present invention will be explained in more detail below by way of Examples, however, is in no way restricted to these Examples.

EXAMPLE 1

To 200 mg of 5,10,11,11a-tetrahydro-9-hydroxy-11-methoxy-8-methyl-5-oxo-1H-pyrrolo-[2,1-C][1,4]-benzodiazepine-2-acrylamide and 2 g of succinic acid anhydride was added 20 ml of pyridine. The mixture was stirred for 30 min at 0° to 4° C. and further for 3 hr at 15° to 30° C. To the reaction mixture was added 200 ml of diethyl ether and the precipitated white crystal was collected by filtration and recrystallized from a dimethylformamide N/10 hydrochloric acid solution to obtain 230 mg of a light yellow crystal of 5,10,11,11a-tetrahydro-9-(3- carboxypropanoyloxy)-11-hydroxy-8-methyl-5-oxo-1H-pyrrolo[2,1-C][1,4]-benzodiazepine-2-acrylamide having a melting point of 262.1° to 263.8° C. This product and equal moles of potassium t-butoxide or sodium methylate were stirred for 20 min at 15° to 30° C. in 5 ml of methanol. Then, the mixture was condensed under reduced pressure and the condensate was recrystallized from a methanol-ethyl acetate solution to obtain a corresponding potassium or sodium salt quantitatively.

Elementary analysis; Calculated for $C_{20}H_{21}N_3O_7$: C, 57.83; H, 5.10; N, 10.12; O, 29.96; Found: C, 57.40; H, 5.23; N, 10.02; O, 27.35.

Infrared absorption spectrum (KBr): 3,300, 3,200, 1,740, 1,710, 1,640 cm$^{-1}$

NMR spectrum (DMSO-d$_6$): 2.27 (3H, s), 2.49 (4H, t, J=20 Hz), 2.72 to 3.20 (2H, m), 3.76 (1H, t, J=9.2 Hz), 5.81 (1H, d, J=15.6 Hz), 5.93 (1H, d, J=9.2 Hz), 7.06 (1H, d, J=8 Hz), 7.26 (1H, d, J=8 Hz), 7.28 (1H, d, J=15.6 Hz), 7.29 (1H, s) ppm

EXAMPLE 2

To 200 mg of 5,10,11,11a-tetrahydro-9-hydroxy- 11-methoxy-8-methyl-5-oxo-1H-pyrrolo-[2,1-C][1,4]-benzodiazepine-2-acrylamide and 2.3 g of glutaric acid anhydride was added 20 ml of pyridine. The mixture was stirred for 30 min at 0° to 4° C. and further for 3 hr at 15° to 30° C. By using this reaction mixture and in accordance with the same manner as in Example 1, recrystallization was conducted to obtain 240 mg of a light yellow crystal of 5,10,11,11a-tetrahydro-9-(4-carboxybutanoyloxy)-11-hydroxy-8-methyl-5-oxo-1H-pyrrolo-[2,1-C][1,4]-benzodiazepine-2-acrylamide having a melting point of 241.2° to 245.3° C. Further, the corresponding sodium and potassium salts were obtained quantitatively.

Elementary analysis; Calculated for $C_{21}H_{23}N_3O_7$: C, 58.74; H, 5.40; N, 9.79; O, 26.08; Found: C, 58.52; H, 6.00; N,9.45; O, 26.03.

Infrared absorption spectrum (KBr): 3,300, 3,150, 1,720, 1,700, 1,635 cm$^{-1}$

NMR spectrum (DMSO-d$_6$): 2.29 (3H, s), 2.34 to 2.65 (6H, m), 2.70 to 3.20 (2H, m), 3.74 (1H, t, J=9 Hz), 5.79 (1H, d, J=15.5 Hz), 5.85 (1H, d, J=9 Hz), 7.02 (1H, d, J=9 Hz), 7.33 (1H, d, J=9 Hz), 7.27 (1H, s), 7.30 (1H, d, J=15 Hz) ppm

EXAMPLE 3

To 200 mg of 5,10,11,11a-tetrahydro-9-hydroxy-11-methoxy-8-methyl-5-oxo-1H-pyrrolo-[2,1-C][1,4]-benzo-diazepine-2-acrylamide and 2.5 g of adipic acid anhydride was added 20 ml of pyridine. The mixture was stirred for 30 min at 0° to 4° C. and further for 3 hr at 15° to 30° C. By using this reaction mixture, recrystallization was conducted in accordance with the same manner as in Example 1 to obtain 240 mg of a yellow crystal of 5,10,11,11a-tetrahydro-9-(5-carboxypentanoyloxy)-11-hydroxy-8-methyl-5-oxo-1H-pyrrolo-[2,1-C][1,4]-benzodiazepine-2-acrylamide having a melting point of 252.3° to 258.7° C. Further, the corresponding sodium and potassium salts were obtained quantitatively.

Elementary analysis; Calculated for $C_{22}H_{25}N_3O_7$: C, 59.59; H, 5.68; N, 9.48; O, 25.25; Found: C, 58.95; H, 5.82; N, 9.21; O 26.02.

Infrared absorption spectrum (KBr): 3,300, 3,160, 1,720, 1,700, 1,640 cm$^{-1}$

NMR spectrum (DMSO-d$_6$): 2.26 (3H, s), 2.30 to 2.65 (8H, m), 2.75 to 3.20 (2H, m), 3.72 (1H, t, J=9.4 Hz), 5.80 (1H, d, J=9.4 Hz), 5.85 (1H, d, J=15.5 Hz), 6.97 (1H, d, J=8.5 Hz), 7.22 (1H, d, J=8.5 Hz), 7.30 (1H, d, J=15.5 Hz), 7.35 (1H, s) ppm

EXAMPLE 4

To 200 mg of 5,10,11,11a-tetrahydro-9-hydroxy-11-methoxy-8-methyl-5-oxo-1H-pyrrolo-[2,1-C][1,4]-benzodiazepine-2-acrylamide and 7 g of nonenylsuccinic acid anhydride was added 40 ml of pyridine. The mixture was stirred for 30 min at 0° to 4° C. and further for 24 hr at 15° to 30° C. Using the reaction mixture, recrystallization was conducted in the same manner as in Example 1 to obtain 200 mg of a yellow crystal of 5,10,11,11a-tetrahydro-9- (3-carboxydodecanoyloxy)-11-hydroxy-8-methyl-5-oxo-1H- pyrrolo-[2,1-C][1,4]-benzodiazepine-2-acrylamide having a melting point of 300.1° to 309.8° C. Further, the corresponding sodium and potassium salts were obtained quantitatively.

Elementary analysis; Calculated for $C_{29}H_{39}N_3O_7$: C, 64.31; H, 7.26; N,7.76; O,20.68; Found: C, 64.03; H, 7.92; N, 7.42; O, 20.63.

Infrared absorption spectrum (KBr): 3,300, 3,200, 1,735, 1,710, 1,640 cm$^{-1}$

NMR spectrum (DMSO-d$_6$): 1.20 to 2.65 (22H, m), 2.29 (3H, s), 2.70 to 3.25 (2H, m), 3.77 (1H, t, J=9 Hz), 5.80 (1H, d, J=15.5 Hz), 5.89 (1H, d, J=9 Hz), 7.02 (1H, d, J=8.2 Hz), 7.33 (1H, d, J=8.2 Hz), 7.36 (1H, d, J=15.5 Hz), 7.37 (1H, s) ppm

EXAMPLE 5

To 200 mg of 5,10,11,11a-tetrahydro-9-hydroxy-11-methoxy-8-methyl-5-oxo-1H-pyrrolo-[2,1-C][1,4]-benzodiazepine-2-acrylamide and 2.2 g of diglycolic acid anhydride was added 20 ml of pyridine. The mixture was stirred for 24 hr at 0° to 4° C. The reaction mixture was subjected to recrystallization in the same manner as in Example 1 to obtain 220 mg of a light yellow crystal of 5,10,11,11a-tetrahydro-9-(4-carboxy-3-oxabutanoyloxy)-11-hydroxy-8-methyl-5-oxo-1H-pyrrolo-[2,1-C][1,4]-benzodiazepine-2-acrylamide having a melting point of 250.3° to 255.5° C. Further, the corresponding sodium and potassium salts were obtained quantitatively.

Elementary analysis; Calculated for $C_{20}H_{21}N_3O_8$; C, 55.68; H, 4.91; N,9.74; O,29.67; Found: C, 55.11; H, 5.24; N, 8.96; O, 30.69.

Infrared absorption spectrum (KBr): 3,300, 3,170, 1,720, 1,700, 1,645 cm$^{-1}$

NMR spectrum (DMSO-d$_6$): 2.28 (3H, s), 2.70 to 3.20 (2H, m), 3.50 to 3.70 (1H, m), 4.20 (4H, s), 5.15 (1H, d, J=6 Hz), 5.80 (1H, d, J=15.6 Hz), 7.02 (1H, d, J=8 Hz), 7.26 (1H, d, J=8 Hz), 7.29 (1H, s), 7.30 (1H, d, J=15.6 Hz) ppm

EXAMPLE 6

To 200 mg of 5,10,11,11a-tetrahydro-9-hydroxy-11-methoxy-8-methyl-5-oxo-1H-pyrrolo-[2,1-C][1,4]-benzodiazepine-2-acrylamide and 2.2 g of S-acetylmercaptosuccinic acid anhydride was added 20 ml of pyridine. The mixture was stirred for 24 hr at 0°to 4° C. The reaction mixture was subjected to recrystallization in the same manner as in Example 1 to obtain 210 mg of a crystal of 5,10,11,11a-tetrahydro-9-(3-carboxy-3-S-acetylmercaptopropanoyloxy)-11-hydroxy-8-methyl-5-oxo-1H-pyrrolo-[2,1-C][1,4]-benzodiazepine-2-acrylamide having a melting point of 262.8° to 266.5° C. Further, the corresponding sodium and potassium salts were obtained quantitatively.

Elementary analysis; Calculated for $C_{22}H_{23}N_3O_8S$: C, 53.98; H, 4.74; N,8.58; O, 26.15; S, 6.55; Found: C, 52.56; H, 4.85; N, 8.24; O. 27.63; S, 6.72.

Infrared absorption spectrum (KBr): 3,300, 3,200, 1,750, 1,725, 1,700, 1,640 cm$^{-1}$ NMR spectrum (DMSO-d$_6$): 2.12 (3H, s), 2.26 (3H, s), 2.40 to 2.60 (3H, m), 2.70 to 3.20 (2H, m), 3.50 to 4.00 (1H, m), 5.62 (1H, d, J=6 Hz), 5.82 (1H, d, J=15.2 Hz), 7.11 (1H, d, J=8 Hz), 7.25 (1H, d, J=8 Hz), 7.28 (1H, s), 7.28 (1H, d, J=15.2 Hz) ppm

EXAMPLE 7

In 10 ml of dimethylformamide were dissolved 200 mg of 5,10,11,11a-tetrahydro-9-hydroxy-11-methoxy-8-methyl-5-oxo-1H-pyrrolo-[2,1-C][1,4]-benzodiazepine-2-acrylamide, 4 g of phthalic acid anhydride and 100 mg of p-toluenesulfonic acid. The solution was stirred for 6 hr at 80° to 100° C. The reaction mixture was cooled down to room temperature and thereto was added 100 ml of N/10 hydrochloric acid. The mixture was allowed to stand for 16 hr at 0° to 4° C. and the resulting white precipitate was collected by filtration and recrystallized from cold methanol to obtain 120 mg of a crystal of 5,10,11,11a-tetrahydro-9-(2-carboxyphenylcarbonyloxy)-11-methoxy-8-methyl-5-oxo-1H-pyrrolo-[2,1-C][1,4]-benzodiazepine-2-acrylamide having a melting point of 353.2° to 355.6° C. Further, from this product, the corresponding sodium and potassium salts were obtained quantitatively in accordance with the manner as shown in Example 1.

Elementary analysis; Calculated for $C_{24}H_{21}N_3O_7$: C, 62.20; H, 4.57; N,9.07; O, 24.17; Found: C, 61.75; H, 4.72; N, 9.13; O, 24.40.

Infrared absorption spectrum (KBr): 3,300, 3,200, 3,050, 1,720 1,700, 1,690, 1,640 cm$^{-1}$ NMR spectrum (DMSO-d$_6$): 2.30 (3H, s), 2.70 to 3.20 (2H, m), 3.80 (1H, t, J=9 Hz), 5.80 (1H, d, J=16 Hz), 6.20 (1H, d, J=9 Hz), 7.00 to 7.55 (8H, m) ppm

EXAMPLE 8

In 10 ml of dimethylformamide were dissolved 200 mg of 5,10,11,11a-tetrahydro-9-hydroxy-11-methoxy-8-methyl-5-oxo-1H-pyrrolo-[2,1-C][1,4]-benzodiazepine-2-acrylamide, 4.4 g of 3-nitrophthalic acid anhydride and 100 mg of p-toluenesulfonic acid. The solution was stirred for 6 hr at 80°to 100° C. The reaction mixture was subjected to recrystallization in the same manner as in Example 7 to obtain 125 mg of a crystal of 5,10,11,11a-tetrahydro-9-(2-carboxy-3-nitrophenylcarbonyloxy)-11-methoxy-8-methyl-5-oxo-1H-pyrrolo-[2,1-C][1,4]-benzodiazepine-2-acrylamide having a melting point of 368.3° to 383.6° C. Further, the corresponding sodium and potassium salts were obtained quantitatively.

Elementary analysis; Calculated for $C_{24}H_{20}N_4O_9$: C, 56.70; H, 3.97; N,11.02; O, 28.32; Found: C, 56.43; H, 4.06; N, 10.85; O, 28.66.

Infrared absorption spectrum (KBr): 3,300, 3,200, 1,725, 1,700, 1,690, 1,645, 1,560, 1,380 $cm^{-1}$ NMR spectrum (DMSO-$d_6$): 2.29 (3H, s), 2.70 to 3.20 (2H, m), 3.77 (1H, t, J=9 Hz), 4.82 (1H, d, J=9 Hz), 5.67 (1H, d, J=15.5 Hz), 7.02 to 7.60 (7H, m) ppm

EXAMPLE 9

In 10 ml of methanol was dissolved 306 mg of 5,10,11,11a-tetrahydro-9-hydroxy-11-methoxy-8-methyl-5-oxo-1pyrrolo-[2,1-C][1,4]-benzodiazepine-2-acrylamide. Thereto were added 420 mg of 3-bromopropylamine and 90 ml of pyridine. The mixture was stirred for 24 hr at 80° C. Then, thereto was added 500 ml of diethyl ether and the resulting yellow crystal was collected by filtration. The crystal collected was dissolved in a small amount of ethanol and applied to a silica gel column (3 cm φ and 50 cm L). Elution was conducted with a chloroform-ethanol mixture (8:2) to obtain an intended fraction. The fraction was concentrated to dryness and the residue was recrystallized from a methanol-ethyl acetate mixture to obtain 282 mg of a light yellow crystal of 5,10,11,11a-tetrahydro-9-(3-aminopropoxy)-11-hydroxy-8-methyl-5-oxo-1H-pyrrolo[2,1-C][1,4]benzodiazepine-2-acrylamide having a melting point of 198° to 201° C.

Elementary analysis; Calculated for $C_{19}H_{24}N_4O_4$: C, 61.28; H, 6.50; N,15.04; O, 17.18; Found: C, 61.48; H, 6.32; N, 15.10; O, 17.10.

Infrared absorption spectrum (KBr-disk): 3,300, 3,200, 2,950, 1,660, 1,240 $cm^{-1}$ NMR spectrum (DMSO-$d_6$): 2.34 (3H, s), 2.30 to 2.63 (6H), 2.72 to 3.18 (2H, m), 4.00 (1H, t, J=9.6 Hz), 5.63 (1H, d, J=8.3 Hz), 5.80 (1H, d, J=14.5 Hz), 6.68 (1H, d, J=8 Hz), 7.23 (1H, d, J=15.8 Hz), 7.25 (1H, d, J=7.9 Hz), 7.29 (1H, s) ppm

EXAMPLE 10

To 100 ml of pyridine were added 200 mg of 5,10,11,11a-tetrahydro-9-hydroxy-11-methoxy-8-methyl-5-oxo-1H-pyrrolo-[2,1-C][1,4]benzodiazepine-2-acrylamide and 210 mg of 1-amino-4-bromohexane. The mixture was stirred for 24 hr at 80° C. The reaction mixture was subjected to recrystallization in the same manner as in Example 1 to obtain 160 mg of a yellow crystal of 5,10, 11, 11a-tetrahydro-9-(4-amino-1-ethylpropoxy)-11-methoxy-8-methyl-5-oxo-1H-pyrrolo-[2,1-C][1,4]benzodiazepine-2-acrylamide having a melting point of 225 to 227° C.

Elementary analysis; Calculated for $C_{23}H_{31}N_4O_4$: C, 64.62; H, 7.31; N,13.10; O,14.97; Found: C, 64.72; H, 7.38; N, 13.05; O, 14.85.

Infrared absorption spectrum (KBr-disk): 3,500, 3,300, 3,200, 2.960, 1,660, 1,250 $cm^{-1}$ NMR spectrum (DMSO-$d_6$): 2.25 (3H, s), 2.32 to 3.15 (14H), 3.45 (3H, s), 4.15 (1H, t, J=10 Hz), 5.42 (1H, d, J=8.7 Hz), 5.78 (1H, d, J=15.1 Hz), 6.73 (1H, d, J=7.8 Hz), 7.24 (1H, d, J=15 Hz), 7.26 (1H, d, J=8.1 Hz) ppm

EXAMPLE 11

In 100 ml of tributylamine were reacted 300 mg of 5,10,11,11a-tetrahydro-9,11-dihydroxy-8-methyl-5-oxo-1H-pyrrolo-[2,1-C][1,4]benzodiazepine-2-acrylamide and 800 mg of 3-chloropropionitrile, for 24 hr at 50° C. After the reaction, 500 ml of diethyl ether was added to obtain a yellowish brown precipitate. To this precipitate was added a small amount of dimethyl sulfoxide to dissolve the precipitate and further a methanol-chloroform mixture (2:8) was added. The resulting solution was applied to a silica gel column (3 cm φ and 50 cm L). Elution was conducted with a methanol-chloroform mixture to obtain an intended fraction. The fraction was concentrated and the residue was recrystallized from an ethanol-water mixture to obtain 272 mg of a yellow crystal of 5,10,11,11a-tetrahydro-9-(2-cyanoethoxy)-11-hydroxy-8-methyl-5-oxo-1H-pyrrolo-[2,1-C][1,4]benzodiazepine-2-acrylamide having a melting point of 218° to 219° C.

Elementary analysis; Calculated for $C_{19}H_{20}N_4O_4$: C, 61.95; H, 5.47; N,15.21; O, 17.37; Found: C, 62.34; H, 5.13; N, 16.10; O, 16.43.

Infrared absorption spectrum (KBr-disk): 3,300, 3,200, 2,930, 2,250, 1,670, 1,255 $cm^{-1}$ NMR spectrum (DMSO-$d_6$): 2.24 (3H, s), 2.45 (2H, t, J=8 Hz), 2.50 (2H, t, J=8.3 Hz), 2.75 to 3.31 (2H, m), 4.30 (1H, t, J=11 Hz), 4.99 (1H, d, J=7.2 Hz), 5.80 (1H, d, J=14.8 Hz), 6.98 (1H, d, J=8.7 Hz), 7.30 (1H, d, J=15.5 Hz), 7.32 (1H, d, J=8.5 Hz), 7.49 (1H,s) ppm

EXAMPLE 12

In 100 ml of tributylamine were stirred 300 mg of 5,10,11,11a-tetrahydro-9,11-dihydroxy-8-methyl-5-oxo-1H-pyrrolo-[2,1-C][1,4]benzodiazepine-2-acrylamide and 800 mg of 4-butyronitrile, for 18 hr at 50° C. After completion of the reaction, 500 ml of diethyl ether was added to obtain a brown precipitate. The precipitate was purified and recrystallized in the same manner as in Example 11 to obtain 303 mg of a yellow crystal of 5,10,11,11a-tetrahydro-9-(2-cyanopropoxy)-11-hydroxy-8-methyl-5-oxo-1H-pyrrolo-[2,1-C][1,4]benzodiazepine-2-acrylamide having a melting point of 211°to 212° C.

Elementary analysis; Calculated for $C_{20}H_{22}N_4O_4$: C, 62.82; H, 5.80; N,14.65; O,16.73; Found: C, 62.94; H, 5.92; N, 15.00; O, 16.04.

Infrared absorption spectrum (KBr-disk): 3,300, 3,200, 2,935, 2,260, 1,670, 1,245 $cm^{-1}$ NMR spectrum (DMSO-$d_6$): 2.20 (3H, s), 2.30 to 2.69 (6H, m), 2.77 to 3.32 (2H, m), 4.31 (1H, t, J=11.3 Hz), 5.04 (1H, d, J=8 Hz), 5.80 (1H, d, J=15 Hz), 7.02 (1H, d, J=8 Hz), 7.31 (1H, d, J=16 Hz), 7.34 (1H, d, J=8.3 Hz), 7.48 (1H, s) ppm

EXAMPLE 13

In 100 ml of tributylamine were reacted 300 mg of 5,10,11,11a-tetrahydro-9,11-dihydroxy-8-methyl-5-oxo-1H-pyrrolo-[2,1-C][1,4]benzodiazepine-2-acrylamide and 900 mg of α-bromo-o-tolunitrile, for 18 hr at 80° C. After completion of the reaction, purification and recrystallization were conducted in the same manner as in Example 11 to obtain 380 mg of a yellow crystal of 5,10,11,11a-tetrahydro-9-(2-cyanobenzyloxy)-11-hydroxy-8-methyl-5-oxo-1H-pyrrolo-[2,1-C][1,4]benzodiazepine-2-acrylamide having a melting point of 283° to 284° C.

Elementary analysis; Calculated for $C_{24}H_{>}N_4O_6$: C, 66.97; H, 5.15; N,13.02; O,14.87; Found: C, 67.20; H, 5.18; N, 13.31; O, 15.31.

Infrared absorption spectrum (KBr-disk): 3,300, 3,200, 3,050, 2,230, 1,680, 1,250 cm$^{-1}$ NMR spectrum (DMSO-d$_6$): 2.20 (3H, s), 2.63 to 3.10 (2H, m), 4.50 (1H, t, J=10.5 Hz), 4.78 (2H, s), 5.31 (7H, d, J=9 Hz), 5.78 (1H, d, J=14.7 Hz), 6.79 (1H, d, J=8.3 Hz), 7.30 (1H, d, J=13.7 Hz), 7.33 (1H, d, J=9.1 Hz), 7.45 (1H, s), 7.50 to 7.70 (4H, m) ppm

EXAMPLE 14

Fifty milliliters of pyridine was added to 200 mg of 5,10,11,11a-tetrahydro-9-hydroxy-11-methoxy-8-methyl-5-oxo-1pyrrolo-[2,1-C][1,4]benzodiazepine-2-acrylamide and 500 mg of monoiodoacetic acid. The mixture was stirred for 5 hr at 50° C. After the reaction, 500 ml of diethyl ether was added to the reaction mixture and the resulting yellow precipitate was collected by filtration. The collected precipitate was dissolved in a small amount of methanol and the solution was applied to a silica gel column (3 cm$\phi$ and 50 cm L). Elution was conducted with a chloroform-methanol mixture (8:2) to obtain an intended fraction. The fraction was concentrated to dryness and the residue was recrystallized from a dimethylformamide-0.1N hydrochloric acid mixture to obtain 180 mg of a light yellow crystal of 5,10,11,11a-tetrahydro-9-carboxymethoxy-11-methoxy-8-methyl-5-oxo-1H-pyrrolo-[2,1-C][1,4]benzodiazepine-2-acrylamide having a melting point of 198 to 201° C. Further, this product was stirred for 20 min at room temperature in equal moles of sodium methylate and 5 ml of methanol. The mixture was concentrated and the residue was recrystallized from a methanol-ethyl acetate mixture to obtain a corresponding sodium salt quantitatively.

Elementary analysis; Calculated for $C_{19}H_{21}N_3O_6$: C, 58.91; H, 5.46; N,10.85; O,24.78; Found: C, 58.72; H, 5.32; N, 11.02; O, 24.95.

Infrared absorption spectrum (KBr-disk): 3,300, 3,200, 1,730, 1,670, 1,240 cm$^{-1}$ NMR spectrum (DMSO-d$_6$): 2.21 (3H, s), 2.65–3.10 (2H, m), 3.25 (3H, s), 3.43 (2H, s), 4.28 (1H, t, J=11 Hz), 5.03 (1H, d, J=7 Hz), 5.81 (1H, d, J=15.5 Hz), 6.83 (1H, d, J=8,3 Hz), 7.26 (1H, d, J=8.5 Hz), 7.28 (1H, d, J=15.6 Hz), 7.29 (1H, s) ppm

EXAMPLE 15

In 25 ml of dimethyl sulfoxide was dissolved 51 mg of 5,10,11,11a-tetrahydro-9-hydroxy-11-methoxy-8-methyl-5-oxo-1H-pyrrolo-[2,1-C][1,4]benzodiazepine-2-acrylamide. Then, thereto were added 63 mg of potassium t-butoxide and 34.2 mg of β-bromopropionic acid. The mixture was stirred for 24 hr at 30° C. After the reaction, 300 ml of diethyl ether was added and the resulting brown precipitate was collected by filtration. The collected precipitate was dissolved in a small amount of methanol and the solution was applied to a silica gel column as used in Example 14. Elution was conducted with a chloroform-methanol mixture (9:2) to obtain an intended fraction. The fraction was concentrated to dryness and the residue was recrystallized from an ethyl acetate-0.1N hydrochloric acid mixture to obtain 40 mg of a crystal of 5,10,11,11a-tetrahydro-9-(2-carboxyethoxy)-11-methoxy-8-methyl-5-oxo-1H-pyrrolo-[2,1-C][1,4]benzodiazepine-2-acrylamide having a melting point of 218° to 220° C. Further, this product was stirred for 30 min at room temperature in equal moles of potassium t-butoxide and 5 ml of methanol. The mixture was concentrated and the residue was recrystallized from a methanol-ethyl acetate mixture to obtain a corresponding potassium salt quantitatively.

Elementary analysis; Calculated for $C_{20}H_{23}N_3O_6$: C, 59.84; H, 5.78; N,10.47; O,23.91; Found: C, 59.05; H, 5.82; N, 10.83; O, 24.30.

Infrared absorption spectrum (KBr-disk): 3,300, 3,200, 2,900, 1,720, 1,660, 1,200 cm$^{-1}$ NMR spectrum (DMSO-d$_6$): 2.20 (3H, s), 2.60 to 3.15 (6H), 3.25 (3H, s), 4.98 (1H, d, J=22 Hz), 5.82 (1H, d, J=15 Hz), 6.54 (1H, d, J=8 Hz), 7.25 (1H, d, 12 Hz), 7.30 (1H, s), 7.43 (1H, d, J=9 Hz) ppm

EXAMPLE 16

In 120 ml of pyridine were reacted 300 mg of 5,10,11,11a-tetrahydro-9-hydroxy-11-methoxy-8-methyl-5-oxo-1H-pyrrolo-[2,1-C][1,4]benzodiazepine and 1 g of 1-(4-carboxyphenyl)-2-chloroethane, for 12 hr at 50° C. After completion of the reaction, purification and recrystallization were conducted in the same manner as in Example 14 to obtain a light yellow crystal of 5,10,11,11a-tetrahydro-9-[2-(4-carboxyphenyl)-ethoxy]-11-methoxy-8-methyl-5-oxo-1H-pyrrolo-[2,1-C][1,4]benzodiazepine-2-acrylamide having a melting point of 193° to 195° C. Further, this product was converted to a corresponding sodium salt in the same manner as in Example 14. The yield of the sodium salt was 350 mg.

Elementary analysis; Calculated for $C_{26}H_{27}N_3O_6$: C, 65.40; H, 5.70; N,8.80; O, 20.10; Found: C, 65.31; H, 5.60; N, 8.72; O, 20.37.

Infrared absorption spectrum (KBr-disk): 3,300, 3,200, 3,050, 2,980, 1,720, 1,685, 1,245 cm$^{-1}$ NMR spectrum (DMSO-d$_6$): 2.23 (3H, s), 2.72 to 3.30 (2H, m), 3.32 (3H, s), 4.03 (1H, t, J=10.5 Hz), 4.91 (2H, t, J=9 Hz), 5.21 (2H, t, J=10.3 Hz), 5.80 (1H, d, J=15.7 Hz), 5.93 (1H, d, J=9.2 Hz), 7.01 (1H, d, J=16.7 Hz), 7.35 (1H, s), 7.40 to 7.70 (4H, m), ppm

What is claimed is:

1. A benzodiazepin compound represented by the following formula or a pharmaceutically acceptable salt thereof:

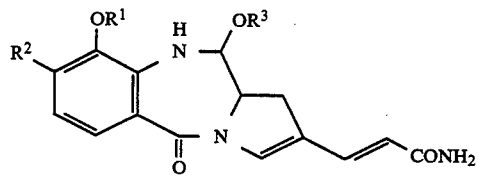

wherein
R$^1$ is —COR$^4$ where R$^4$ is —Y—COOH or —Y'—O—Y"—COOH in which Y, Y' and Y" are independently a C$_{1-15}$ alkylene group or a phenylene group, a C$_{1-8}$ alkyl group or a phenyl —C$_{1-4}$ alkyl group having a substituent selected from a carboxyl group, an amino group and a cyano group,
R$^2$ is a lower alkyl group, and
R$^3$ is a hydrogen atom or a lower alkyl group.

2. A benozodiazepine compound according to claim 1, wherein the alkylene group is methylene, ethylene, propylene, trimethylene, butylene or tetramethylene.

3. A benzodiazepine compound according to claim 1, wherein the lower alkyl group is methyl, ethyl, n-propyl, i-propyl, n-butyl or i-butyl.

4. 5,10,11,11a-Tetrahydro-9-(3-carboxypropanoyloxy)-11-hydroxy-8-methyl-5-oxo-1H-pyrrolo-[2,1-C][1,4]benzodiazepine-2-acrylamide, and its alkali and alkaline earth metal salts.

5. 5,10,11,11a-Tetrahydro-9-(4-carboxybutanoyloxy)-11-hydroxy-8-methyl-5-oxo-1H-pyrrolo-[2,1-C][1,4]benzodiazepine-2-acrylamide, and its alkali and alkaline earth metal salts.

6. 5,10,11,11a-Tetrahydro-9-(5-carboxypentanoyloxy)-11-hydroxy-8-methyl-5-oxo-1H-pyrrolo-[2,1-C][1,4]benzodiazepine-2-acrylamide, and its alkali and alkaline earth metal salts.

7. 5,10,11,11a-Tetrahydro-9-(3-carboxydodecanoyloxy)-11-hydroxy-8-methyl-5-oxo-1H-pyrrolo-[2,1-C][1,4]benzodiazepine-2-acrylamide, and its alkali and alkaline earth metal salts.

8. 5,10,11,11a-Tetrahydro-9-(4-carboxy-3-oxabutanoyloxy)-11-hydroxy-8-methyl-5-oxo-1H-pyrrolo-[2,1-C][1,4]-benzodiazepine-2-acrylamide, and its alkali and alkaline earth metal salts.

9. 5,10,11,11a-Tetrahydro-9-(3-carboxy-3-S-acetylmercaptopropanoyloxy)-11-hydroxy-8-methyl-5-oxo-1H-pyrrolo-[2,1-C][1,4]benzodiazepine-2-acrylamide, and its alkali and alkaline earth metal salts.

10. 5,10,11,11a-Tetrahydro-9-(2-carboxyphenyl-carbonyloxy)-11-methoxy-8-methyl-5-oxo-1H-pyrrolo-[2,1-C][1,4]benzodiazepine-2-acrylamide, and its alkali and alkaline earth metal salts.

11. 5,10,11,11a-Tetrahydro-9-(2-carboxy-3-nitrophenylcarbonyloxy)-11-methoxy-8-methyl-5-oxo-1H-pyrrolo-[2,1-C][1,4]-benzodiazepine-2-acrylamide, and its alkali and alkaline earth metal salts.

12. 5,10,11,11a-Tetrahydro-9-(3-aminopropoxy)-11-hydroxy-8-methyl-5-oxo-1H-pyrrolo-[2,1-C][1,4]-benzodiazepine-2-acrylamide, and its alkali and alkaline earth metal salts.

13. 5,10,11,11a-Tetrahydro-9-(4-amino-1-ethylpropoxy)-11-methoxy-8-methyl-5-oxo-1H-pyrrolo-[2,1-C][1,4]-benzodiazepine-2-acrylamide, and its alkali and alkaline earth metal salts.

14. 5,10,11,11a-Tetrahydro-9-(2-cyanoethoxy)-11-hydroxy-8-methyl-5-oxo-1H-pyrrolo-[2,1-C][1,4]benzodiazepine-2-acrylamide and its alkali and alkaline earth metal salts.

15. 5,10,11,11a-Tetrahydro-9-(3-cyanopropoxy)-11-hydroxy-8-methyl-5-oxo-1H-pyrrolo-[2,1-C][1,4]benzodiazepine-2-acrylamide, and its alkali and alkaline earth metal salts.

16. 5,10,11,11a-Tetrahydro-9-(2-cyanobenzyloxy)-11-hydroxy-8-methyl-5-oxo-1H-pyrrolo-[2,1-C][1,4]benzodiazepine-2-acrylamide and its alkali and alkaline earth metal salts.

17. 5,10,11,11a-Tetrahydro-9-carboxymethoxy-11-methoxy-8-methyl-5-oxo-1H-pyrrolo-[2,1-C][1,4]benzodiazepine-2-acrylamide, and its alkali and alkaline earth metal salts.

18. 5,10,11,11a-Tetrahydro-9-(2-carboxyethoxy)-11-methoxy-8-methyl-5-oxo-1H-pyrrolo-[2,1-C][1,4]benzodiaepine-2-acrylamide, and its alkali and alkaline earth metal salts.

19. 5,10,11,11a-Tetrahydro-9-[2-(4-carboxyphenyl)-ethoxy]-11-methoxy-8-methyl-5-oxo-1H-pyrrolo-[2,1-C][1,4]-benzodiazepine-2-arylamide, and its alkali and alkaline earth metal salts.

* * * * *